(12) United States Patent
Ihm et al.

(10) Patent No.: US 6,376,562 B1
(45) Date of Patent: Apr. 23, 2002

(54) HYBRID CATALYST FOR HYDROCARBON SYNTHESIS VIA HYDROGENATION OF CARBON DIOXIDE

(75) Inventors: Son-Ki Ihm, Seoul; Young-Kwon Park, Kwangju; Jong-Ki Jeon, Chungchongnam-do; Kwang-Eun Jeong, Inchon, all of (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 0 days.

(21) Appl. No.: 09/409,272

(22) Filed: Sep. 30, 1999

(30) Foreign Application Priority Data

Dec. 24, 1998 (KR) .............................................. 98-58447

(51) Int. Cl.$^7$ ............................ B01J 29/85; B01J 23/72; C07C 27/06
(52) U.S. Cl. ...................... 518/713; 518/714; 502/305; 502/343; 502/345; 502/214
(58) Field of Search ................ 502/208, 214, 502/305, 343, 345; 518/713, 714

(56) References Cited

U.S. PATENT DOCUMENTS

| | | | |
|---|---|---|---|
| 3,326,956 A | * 6/1967 | Davies et al. | |
| 4,663,355 A | * 5/1987 | Coughlin | 518/713 |
| 4,873,390 A | * 10/1989 | Lewis et al. | 585/638 |
| 5,714,662 A | * 2/1998 | Vora et al. | 585/640 |
| 5,817,906 A | * 10/1998 | Marker et al. | 585/640 |
| 6,127,432 A | * 10/2000 | Wegman et al. | 518/715 |

OTHER PUBLICATIONS

Masahiro Fujiwara et al., Development of Composite Catalysts Made of Cu–Zn–Cr oxide/zeolite for the Hydrogenation of Carbon Dioxide, Applied Catalysis A: General, 121: 113–124 (1995).
Kaoru Fujimoto et al., Hydrogenation of Carbon Monoxide on Carbon Monoxide Reducing Catalyst and Solid Acid. 6. Selective Production of C3 and C4 Hydrocarbons from Synthesis Gas, Ind. Eng. Chem. Res., 27: 920–926 (1988).
Clarence D. Chang et al., Syngas Conversion to Ethane over Metal–/Zeolite Catalysts, J. Catalysis, 90:84–87 (1984).

* cited by examiner

*Primary Examiner*—Steven P. Griffin
*Assistant Examiner*—Christina Ildebrando
(74) *Attorney, Agent, or Firm*—Knobbe Martens Olson & Bear LLP.

(57) ABSTRACT

The present invention provides a hybrid catalyst which is prepared by mixing a methanol synthesis catalyst with SAPO-type zeolite as a methanol conversion catalyst, and a process for the preparation of hydrocarbons from carbon dioxide by using the hybrid catalyst. The hybrid catalyst of the invention can be used for preparing hydrocarbons having a carbon number of more than 2 from carbon dioxide under a relatively on the hydrocarbons produced. Therefore, the hybrid catalyst may be used for preparing various high-valued hydrocarbons from an ubiquitous carbon source of carbon dioxide.

13 Claims, No Drawings

HYBRID CATALYST FOR HYDROCARBON SYNTHESIS VIA HYDROGENATION OF CARBON DIOXIDE

BACKGROUND OF THE INVENTION

1. Field of the Invention

The present invention relates to a hybrid catalyst, more specifically, to a hybrid catalyst which is prepared by mixing a methanol synthesis catalyst with SAPO-type zeolite as a methanol conversion catalyst, and a process for the preparation of hydrocarbons from carbon dioxide by using the hybrid catalyst.

2. Background of the Invention

In general, hydrocarbons are synthesized from carbon oxides such as carbon monoxide or carbon dioxide via hydrogenation by employing hybrid catalysts, that are prepared by mixing a catalyst for the synthesis of methanol, an intermediate in the process of preparing hydrocarbons from the carbon oxides, with a methanol conversion catalyst.

For example, Chang et al. synthesized hydrocarbons via hydrogenation of carbon monoxide by employing Cr/Zn/Al as the methanol synthesis catalyst and HZSM-5 as the methanol conversion catalyst, respectively(see: C. D. Chang et al., J. Catal., 90:84, 1984). Also, Fujimoto et al. reported that hydrocarbons can be made from carbon monoxide by using a hybrid catalyst prepared by mixing a methanol synthesis catalyst such as $Pd/SiO_2$ or Cu/Zn with a methanol conversion catalyst such as HZSM-5 and H-Mordenite(see: K. Fujimoto et al., I & EC Res., 27:920, 1988).

As described above, many efforts have been made to prepare hydrocarbons via hydrogenation of carbon monoxide, while hydrogenation of carbon dioxide has not been successfully accomplished, since the carbon dioxide is a more stable chemical in terms of thermodynamics than carbon monoxide.

Carbon dioxide is one of the most abundant carbon sources and its concentration is continuously increased in the atmosphere, which plays a critical role in causing the greenhouse effect on Earth. For this reason, it is urgently needed to develop a method for converting carbon dioxide to high-valued chemical compounds such as methanol and hydrocarbons, as an approach to overcome the limitation of carbon sources and also improve the air environment on Earth.

Under this circumstance, Fujimoto et al. successfully synthesized hydrocarbons from carbon dioxide by using a hybrid catalyst comprising a methanol synthesis catalyst such as Cu/Zn or Zn/Cr, and a methanol conversion catalyst such as DAY(see: K. Fujimoto et al., Appl. Catal., 31:13, 1987), although the yield of hydrocarbons is very limited (yield=4.1% (w/w)).

Thereafter, Inui et al. synthesized hydrocarbons from carbon dioxide, by using a hybrid catalyst made of Cu/Cr/Zn and HZSM-5 at 50 atm and 320° C.(see: T. Inui et al., Appl. Catal., 94:31, 1993), and Fujiwara et al., by using a hybrid catalyst composed of Cu/Zn/Cr and Y zeolite(see: M. Fujiwara et al., Appl. Catal., A:General, 121:133, 1995). However, the prior art catalysts have revealed some shortcomings in the senses that: they are not appropriate to synthesize the higher alkanes, since the reactions are generally terminated to produce ethane only, the yields of hydrocarbons are very limited.

Although numerous researchers have continuously made efforts in order to develop catalysts available for producing hydrocarbons via hydrogenation of carbon monoxide, carbon dioxide, etc., the prior art hybrid catalysts comprising HZSM-5, Y zeolite, etc. as the methanol conversion catalyst provide low yield of hydrocarbons. In addition, only limited kinds of hydrocarbons can be prepared by employing the catalysts and a high pressure of more than 50atm is essentially accompanied by the reaction.

Under these circumstances, there are strong reasons for exploring and developing a novel hybrid catalyst which can produce hydrocarbons in a high yield, while allowing the production of various hydrocarbons.

SUMMARY OF THE INVENTION

The present inventors have made an effort to solve the problems of the prior art hybrid catalysts to produce hydrocarbons from carbon dioxide, and they prepared a novel hybrid catalyst by mixing a methanol synthesis catalyst with zeolite SAPO-type which is a methanol conversion catalyst, and discovered that hydrocarbons can be synthesized from carbon dioxide by using the hybrid catalyst in a high yield under a relatively mild condition.

A primary object of the present invention is, therefore, to provide a hybrid catalyst for production of hydrocarbons from carbon dioxide.

The other object of the invention is to provide a process for preparing hydrocarbons from carbon dioxide by using the hybrid catalyst.

DETAILED DESCRIPTION OF THE INVENTION

A hybrid catalyst for production of hydrocarbons from carbon dioxide of the present invention is prepared by mixing a methanol synthesis catalyst and a methanol conversion catalyst of SAPO-type zeolite. The hybrid catalyst of the invention allows the synthesis of hydrocarbons having a carbon number of more than 2 in a high yield under a low pressure.

The hybrid catalyst of hte invention isexplained in more detail as below.

The present inventors prepared a $Cu/ZnO/ZrO_2$ catalyst as the methanol synthesis catalyst by the conventional coprecipitation method in the art. The $Cu/ZnO/ZrO_2$ catalysts contains: Cu of 10 to 60% (w/w); ZnO, 0 to 30% (w/w); and, $ZrO_2$ 10 to 90% (w/w), most preferably Cu, 60% (w/w); ZnO, 30% (w/w); and $ZrO_2$, 10% (w/w), respectively. And then, SAPO-5 and SAPO-34, which are SAPO-type zeolites, are employed as the methanol conversion catalyst. The hydrogen ion outside of lattice in the SAPO-5 and SAPO-34 zeolites may be substituted for copper ion, where the content of copper is 0.5 to 2% (w/w), preferably 1 to 2% (w/w). The hybrid catalyst of the present invention may be prepared by mixing a methanol synthesis catalyst such as $Cu/ZnO/ZrO_2$, $Cr_2O_3/ZnO/Al_2O_3$, $Pd/SiO_2$, Cu/ZnO, $ZnO/Cr_2O_3$ and $Cu/Cr_2O_3/ZnO$ catalysts with a methanol conversion catalyst of SAPO-type zeolites which may contain Cu optionally, where the methanol synthesis catalyst and the SAPO-type zeolite are mixed in a ratio of 1:4 to 4: 1(w/w), most preferably 1:1 (w/w).

A process for preparing hydrocarbons from carbon dioxide by using the hybrid catalyst of the invention is illustrated in more detail as followings.

The process for preparing hydrocarbons from carbon dioxide comprises the steps of: reducing a hybrid catalyst by placing the hybrid catalyst prepared by the invention in a high pressure reactor, purging $H_2/Ar$, elevating the temperature of the reactor to reach 250 to 350° C. gradually under atmospheric pressure, and increasing the concentration of hydrogen gas to 100%; and, hydrogenising carbon dioxide to give hydrocarbons by pressurizing the reactor to reach 25 to 35atm by purging helium gas to the reactor, purging $CO_2$ and $H_2$, to maintain $H_2/CO_2$ of 3 and W/F of 10 to 30 g-cat h/mol, and elevating the temperature of the reactor to reach 350 to 500° C.

The products are analyzed by the aid of gas chromatography connected with the said reactor to examine the conversion of carbon dioxide and the yield of hydrocarbons. As a result, it was determined that hydrocarbons having a carbon number of more than 2 were synthesized in a high yield under a relatively low pressure. In particular, hybrid catalysts comprising a methanol conversion catalyst of SAPO-34 and SAPO-5 revealed to have a high selectivity on propane and butane, respectively. Also, it was found that the activity of the hybrid catalyst is increased by substituting copper ion for hydrogen ion outside of the lattice in the said SAPO-type zeolites.

The present invention is further illustrated in the following examples which should not be taken to limit the scope of the invention.

Example 1
Preparation of a Methanol Synthesis Catalyst

A methanol synthesis catalyst which comprises a major component of copper ion, was prepared by the conventional coprecipitation method for preparing methanol synthesis catalyst: Metal containing solution was first prepared by adding copper, zinc and zirconium in nitrate or acetate form to distilled water in a proper amount, to contain $Cu:ZnO:ZrO_2$ of 6:3:1 (w/w/w). And then, the metal containing solution and 0.6N NaOH solution as a precipitating agent were added in a dropwise to the distilled water heated to 80° C., and the reaction solution was stirred for 1 h while maintaining the temperature and pH of 80° C. and 7.0±0.3, respectively. Then, the reaction solution was cooled to room temperature and filtered with Buchner funnel, and washed with deionized water to give Cu/Zn/Zr precipitate free of Na. The Cu/Zn/Zr precipitate was dried for 12 hrs in the air at 110° C. and calcined at 350° C. for 12 hrs to prepare $Cu/ZnO/ZrO_2$ catalyst in which the weight ratio of $Cu/ZnO/ZrO_2$ is 6:3:1

Example 2
Preparation of a Methanol Conversion Catalyst

Example 2-1
Preparation of SAPO-5 and SAPO-34

SAPO-5 w as prepared by the conventional method in the art(see: U.S. Pat No. 4,440,871): $H_3PO_4$ was first added to distilled water and stirred vigorously. To the $H_3PO_4$ solution was added pseudoboehmite or aluminum isopropoxide and stirred to reach a homogeneous state, and colloidal silica (Ludox HS-40, DuPont, USA) was subsequently added to the said solution and mixed sufficiently. Then, a templating agent of tripropylamine(TPA) was added, and crystallized in an autoclave maintaining 200° C. for about 48 hrs. The crystals thus obtained were washed with distilled water several times and dried at the temperature of 110° C. Finally, the resultant was calcined at 550° C. to obtain SAPO-5.

Meanwhile, SAPO-34 was prepared in an analogous manner as described above, except for using morpholine as a templating agent instead of TPA.

Example 2-2
Preparation of Cu/SAPO-5 and Cu/SAPO-34

Cu/SAPO-5 and Cu/SAPO-34 were prepared by substituting 1.7% (w/w) of copper ion for hydrogen ion outside of SAPO-5 and SAPO-34 lattice prepared in Example 2-1, by the aid of ion-exchange method employing copper nitrate.

Example 3
Preparation of Hybrid Catalysts 4 kinds of hybrid catalysts were prepared by mixing the same weights of the methanol synthesis catalyst of $Cu/ZnO/ZrO_2$ obtained in Example 1, and the methanol conversion catalyst of SAPO-34, SAPO-5, Cu/SAPO-34 or Cu/SAPO-5 obtained in Examples 2-1 to 2-2.

Example 4
Synthesis of Hydrocarbons from Carbon Dioxide

By using the hybrid catalysts prepared i n Example 3, hydrogenation reaction was carried out in and autoclave under a condition of 28 atm, $H_2/CO_2=3$ and W/F=20 g-cat·h/mol: The hybrid catalysts were first reduced by placing each of hybrid catalysts in a high pressure reactor, purging $H_2/Ar$ 5%(v/v) gas, elevating the temperature of the reactor to reach 280° C. gradually under atmospheric pressure, and increasing the concentration of hydrogen gas gradually to reach 10, 20, 40 and 100% at an interval of 30 min. Then, the reactor was pressurized to reach 28 atm by purging helium gas, and reactants of $CO_2$ and $H_2$ were injected to maintain $H_2/Co_2$ of 3 and W/F of 10 to 30 g-cat·h/mol. And than, the temperature of the reactor was elevated to reach 350 to 400° C. depending on the kinds of catalysts.

Finally, the products were analyzed by gas chromatography connected with the reactor where TCD and FID detector were equipped to examine the conversion of carbon dioxide and the yield of each hydrocarbon. Table 1 summarizes the reaction of conversion of carbon dioxide, yield of hydrocarbons, selectivity of hydrocarbons having various carbon numbers and yield of the hydrocarbons, respectively.

TABLE 1

Hydrogenation of carbon dioxide using the hybrid catalysts of the present invention

| Catalyst | Cu/ZnO/ ZrO$_2$ + SAPO-5 | Cu/ZnO/ ZrO$_2$ + Cu/SAPO-5 | Cu/ZnO/ ZrO$_2$ + SAPO-34 | Cu/ZnO/ ZrO$_2$ + Cu/SAPO-34 |
|---|---|---|---|---|
| Reaction Temperature | 350°C. | 350°C. | 400°C. | 400°C. |
| Conversion rate of CO$_2$ (%) | 31.8 | 37.8 | 34.5 | 40.2 |
| Yield (wt, %) | | | | |
| H.C.* | 9.1 | 14.9 | 11.0 | 15.8 |
| CO | 21.0 | 21.5 | 23.0 | 23.6 |
| MeOH | 1.6 | 1.2 | 0.5 | 0.8 |
| DME** | 0.1 | 0.2 | 0.0 | 0.0 |
| Selectivity of hydrogencarbons (wt, %) | | | | |
| C$_1$ | 4.0 | 3.6 | 3.6 | 1.9 |
| C$_2$ | 12.7 | 11.2 | 34.8 | 31.4 |
| C$_3$ | 33.0 | 25.2 | 52.0 | 55.2 |
| C$_4$ | 43.3 | 48.5 | 8.8 | 12.1 |
| C$_5$ | 5.0 | 7.5 | 0.7 | 0.7 |
| C$_6$ | 1.9 | 4.0 | 0.1 | 0.1 |
| Yield of C$_{2+}$ (wt, %) | 8.8 | 14.4 | 10.6 | 15.5 |

*H.C. (hydrocarbon)
**DME (dimethylether)

As can be seen in Table 1 above, it was determined that the productivity of hydrocarbons over $C_2$ could be significantly improved by using the hybrid catalysts of the invention. Particularly, the hybrid catalysts comprising SAPO-34 or Cu/SAPO-34 found to show a high selectivity on propane, while the hybrid catalysts comprising SAPO-5 or Cu/SAPO-5 to show a high selectivity on butane. This results suggested that: the selectivity on the hydrocarbons produced from hydrogenation reaction can be controlled easily by varying the methanol conversion catalyst of SAPO-type zeolite which is one of components of the hybrid catalyst; and, the addition of copper to SAPO-type zeolite can increase the activity of the hybrid catalyst, finally to improve the productivity of hydrocarbons.

As clearly illustrated and demonstrated as above, the present invention provides a hybrid catalyst for production of hydrocarbons from carbon dioxide. The hybrid catalyst of the invention can be used for preparing hydrocarbons having a carbon number of more than 2 from carbon dioxide under a relatively low pressure, with a high yield and selectivity on the hydrocarbons produced. Therefore, the hybrid catalyst may be used for preparing various high-valued hydrocarbons from an ubiquitous carbon source of carbon dioxide.

What is claimed is:

1. A hybrid catalyst comprising a methanol synthesis catalyst and a methanol conversion catalyst, wherein the methanol conversion catalyst comprises a SAPO catalyst selected from the group consisting of Cu/SAPO-5 and Cu/SAPO-34, wherein each of the Cu/SAPO-5 and Cu/SAPO-34 contains 0.5 to 2% (w/w) Cu.

2. The hybrid catalyst of claim 1, wherein the methanol synthesis catalyst is $Cu/ZnO/ZrO_2$, $Cr_2O_3/ZnO/Al_2O_3$, $Pd/SiO2$, $Cu/ZnO$, $ZnO/Cr_2O_3$ or $Cu/Cr_2O_3/ZnO$.

3. The hybrid catalyst of claim 1, wherein the methanol synthesis catalyst and the methanol conversion catalyst are in a ratio of 4:1 to 1:4 by weight.

4. A process of making the hybrid catalyst of claim 1, comprising:

preparing the SAPO catalyst, wherein the preparation comprises ion-exchanging SAPO-5 or SAPO-34 catalyst with copper nitrate;

preparing the methanol synthesis catalyst; and mixing the SAPO catalyst and the methanol synthesis catalyst.

5. A process for producing hydrocarbons from carbon dioxide, comprising:

providing the hybrid catalyst of claim 1; and contacting the hybrid catalyst with carbon dioxide and hydrogen so as to hydrogenate carbon dioxide.

6. The process of claim 5, wherein the contacting is performed at a pressure of 25–35 atm.

7. The process of claim 5, wherein the contacting is performed at a temperature of 250–500° C.

8. The process of claim 7, wherein the temperature ranges from 350–500° C.

9. A hybrid catalyst comprising a methanol synthesis catalyst and a methanol conversion catalyst, wherein the methanol synthesis catalyst comprises a $Cu/ZnO/ZrO_2$ catalyst, and wherein the methanol conversion catalyst comprises Cu/SAPO-5 or Cu/SAPO-34, wherein each of the Cu/SAPO-5 and Cu/SAPO-34 contains 0.5 to 2% (w/w) Cu.

10. The hybrid catalyst of claim 9, wherein the $Cu/ZnO/ZrO_2$ catalyst contains 10 to 60% (w/w) Cu, 0 to 30% (w/w) ZnO and 10 to 90% (w/w) $ZrO_2$.

11. The hybrid catalyst of claim 9, wherein the methanol synthesis catalyst and the methanol conversion catalyst are in a ration of 4:1 to 1:4 by weight.

12. A process of making the hybrid catalyst of claim 9, comprising:

preparing the SAPO catalyst and the methanol synthesis catalyst; and mixing the SAPO catalyst and the methanol synthesis catalyst.

13. A process for producing hydrocarbons from carbon dioxide, comprising:

providing the hybrid catalyst of claim 9, and contacting the hybrid catalyst with carbon dioxide and hydrogen so as to hydrogenate carbon dioxide.

* * * * *

UNITED STATES PATENT AND TRADEMARK OFFICE
CERTIFICATE OF CORRECTION

PATENT NO.    : 6,376,562 B1
DATED         : April 23, 2002
INVENTOR(S)   : Ihm et al.

It is certified that error appears in the above-identified patent and that said Letters Patent is hereby corrected as shown below:

<u>Column 6,</u>
Line 22, please replace "ration" with -- ratio --.

Signed and Sealed this

Tenth Day of June, 2003

JAMES E. ROGAN
*Director of the United States Patent and Trademark Office*